United States Patent [19]
Paciorek et al.

[11] Patent Number: 4,581,468
[45] Date of Patent: Apr. 8, 1986

[54] BORON NITRIDE PRECERAMIC POLYMERS

[75] Inventors: Kazimiera J. L. Paciorek, Corona del Mar; Reinhold H. Kratzer, Irvine; David H. Harris, Sierra Madre; Mark E. Smythe, Pasadena; Patrick F. Kimble, Corona del Mar, all of Calif.

[73] Assignee: Ultrasystems, Inc., Irvine, Calif.

[21] Appl. No.: 733,457

[22] Filed: May 13, 1985

[51] Int. Cl.$^4$ .......................... C07F 7/10; C07F 7/02; C04B 35/58; C01B 21/064
[52] U.S. Cl. .................................. 556/403; 423/290; 501/96
[58] Field of Search ..................... 556/403; 423/290; 501/96

[56] References Cited
U.S. PATENT DOCUMENTS
3,382,279  5/1968  Horn et al. ........................ 556/403

OTHER PUBLICATIONS
Mikhailov et al., "Izvestia Akad. Nauk.", USSR, 4/1963, pp. 641–645.

Primary Examiner—Paul F. Shaver
Attorney, Agent, or Firm—Hubbard, Stetina & Brunda

[57] ABSTRACT

B-triamino-N-tris(trialkylsilyl)borazines, their condensation products, and the transformation of these into preceramic polymers amenable to fiber drawing and ultimately boron nitride fiber formation.

8 Claims, No Drawings

BORON NITRIDE PRECERAMIC POLYMERS

RIGHTS OF THE GOVERNMENT

The invention described herein may be manufactured and used by or for the Government of the United States for all governmental purposes without the payment of any royalty.

FIELD OF THE INVENTION

The invention relates to B-triamino-N-tris(trialkylsily)borazines, their condensation products, and final transformation into carbon-free boron nitride.

BACKGROUND OF THE INVENTION

This invention relates to novel compositions of matter as represented by B-triamino-N-tris(trimethylsilyl)borazine and its transformation into polymeric materials to be used as ceramics precursors. Ceramics such as BN, $B_4C$, SiC, and $Si_3N_4$ are of great importance commercially. However, due to their insolubility and nonfusibility, the processing of these materials into useful end products presents grave difficulties. A material which can be transformed into a readily processible polymer prior to final pyrolysis into a ceramic offers a potential for ceramic fiber production, coatings, foams, and also as a binder for ceramic powders eliminating the use of additives (i.e. sintering aids). It is the principal object of this invention, therefore, to provide a material amenable to transformation into preceramic polymers.

Another object of the invention is to provide a process for obtaining boron nitride fibers.

Other objects and advantages of the invention will become apparent to those skilled in the art upon consideration of the accompanying disclosure.

SUMMARY OF THE INVENTION

The present invention resides in the synthesis of B-triamino-N-tris(trialkylsilyl)borazines and their condensation products, namely dimers, tetramers, and octamers, as represented by the general formulae shown

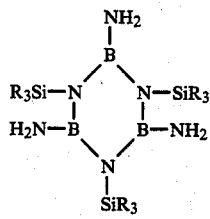

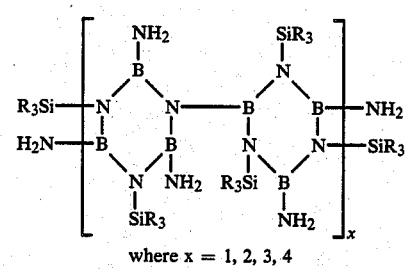

where x = 1, 2, 3, 4

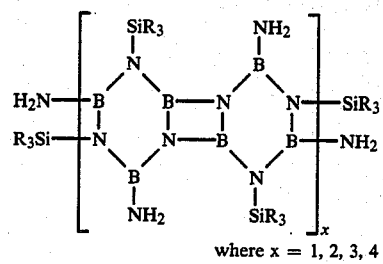

where x = 1, 2, 3, 4

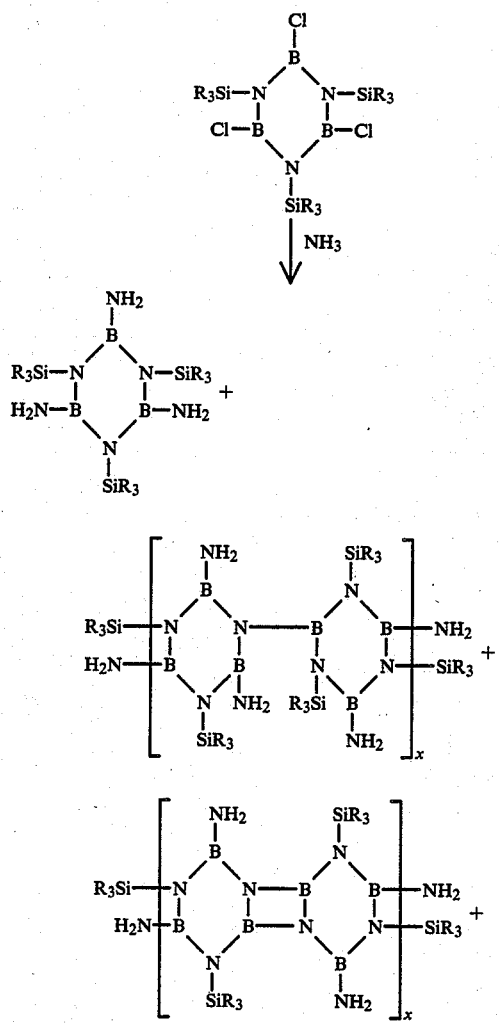

wherein R is an alkyl group such as methyl, ethyl, propyl, and butyl having the formula $C_nH_{2n+1}$.

The following equation represents the synthesis process:

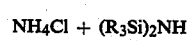

$NH_4Cl + (R_3Si)_2NH$

The procedure followed in the synthesis of the above materials consists of an interaction of B-trichloro-N-tris(trialkylsilyl)borazine, a material described by P. Geymayer, E. G. Rochow, and U. Wannagat in *Angewante Chemie Internat. Edit.* 3, 633 (1964), with ammonia. This reaction is usually conducted at temperatures ranging from $-78°$ to $25°$ C. The reaction period ranges from 4 to 24 hr., although longer or shorter periods can be used. The reaction is carried out under an inert gas such as nitrogen, helium, or argon. In general, ammonia is used in 2 to 10 fold excess over what is required. Subsequent condensation to the preceramic polymer is accomplished at temperatures ranging from 50° to 300° C. over a period of 8 to 250 hr. both in an inert gas such as nitrogen, helium, or argon, or in vacuo. To obtain final boron nitride articles such as fibers, the preceramic fibers are drawn from the melt, although the polymer is also amenable to solution fiber spinning. The preceramic fibers are then transformed to boron nitride fibers by heating in gaseous ammonia at temperatures increased gradually from 60° to 1000° C. over time periods ranging from 8 hr. to 27 days.

A more complete understanding of the invention can be obtained by referring to the following illustrative examples which are not intended, however, to be unduly limitative of the invention.

EXAMPLE I

Preparation of B-triamino-N-tris(trimethylsilyl)borazine and condensation products thereof Under nitrogen by-pass to liquid ammonia (20 ml) in a three-neck 100 ml flask equipped with a Dry Ice condenser and addition funnel was added B-trichloro-N-tris(trimethylsily)borazine (10.0 g, 24.98 mmol) in hexane (50 ml) over a period of 1.6 hr. The addition was accompanied by the formation of a white precipitate. Subsequently, the mixture was allowed to warm slowly to room temperature. Filtration in an inert atmosphere gave 4.04 g (100% yield) of ammonium chloride. The filtrate, after removal of the solvent, gave the crude B-triamino-N-tris(trimethylsilyl)borazine (7.38 g, 86% yield). A 6.60 g portion was subjected to in vacuo distillation at 135° C. which resulted in the removal of a by-product, bp 75°–87° C. (1.05 g, 15.9%). The semi-liquid residue (4.80 g) consisted of a 2:1 mixture of the doubly bridged borazine dimers and tetramers. Anal. calcd. for $C_{14}H_{51.33}N_{12.67}B_8Si_{4.67}$: B, 14.06%; N, 28.86%; MW, 615. Found: B, 13.46%; N, 26.76%; MW, 620. To achieve further condensation to preceramic polymer the above mixture of dimers and tetramers was subjected to heat treatments at 196° to 260° C. Details of these treatments are given in Table I.

TABLE I
STEPWISE DEGRADATION OF B—TRIAMINO-N—TRIS(TRIMETHYLSILYL)BORAZINE

| Temp °C. | Duration hr. | Volatiles % theory | Polymer MW | mp °C. |
|---|---|---|---|---|
| −78 to 135 | n.a. | 41.6 | 620 | — |
| 196–210 | 53 | 9.5 | n.d. | — |
| 250–260 | 4 | 1.1 | 1010 | 125–140 (soft 80) |

The preceramic polymer consisted of a mixture of doubly-bridged tetramers and octamers. Anal. calcd. for $C_{22}H_{80.67}N_{23.33}B_{16}Si_{7.33}$: B, 16.46%; N, 31.09%; MW, 1051. Found: B, 16.01%; N, 29.39%; MW, 1010.

EXAMPLE II

Boron nitride fiber production

From the preceramic polymer described in Example I, fibers were melt-drawn at 120°–160° C. The preceramic fibers were subsequently cured and transformed into boron-nitride ceramic fibers by gradual heating in ammonia atmosphere from 60°–970° C. over a period of 12 days. The fibers thus produced were completely colorless, free of carbon, and did not melt or lose any weight when heated in nitrogen at 1000° C.

As will be evident to those skilled in the art, modifications of the present invention can be made in view of the foregoing disclosure without departing from the spirit and scope of the invention.

We claim:

1. B-triamino-N-tris(trialkylsilyl)borazines

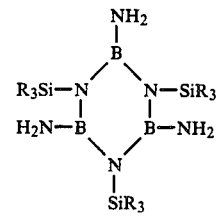

wherein R is methyl, ethyl, or butyl of the general formula $C_nH_{2n+1}$.

2. B-triamino-N-tris(trimethylsilyl)borazine

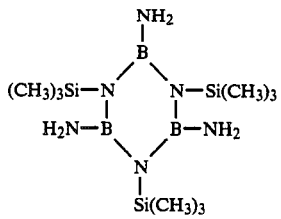

3. Condensed B-triamino-N-tris(trialkylsilyl)borazines, singly and doubly bridged and mixtures thereof

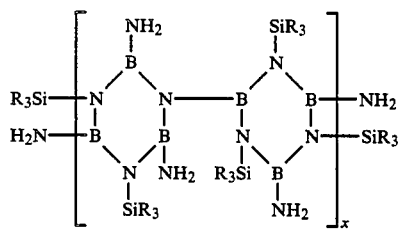

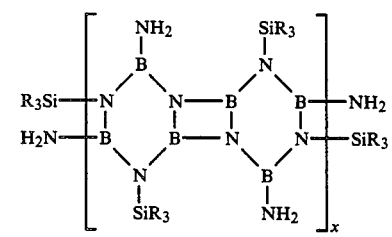

where R is methyl, ethyl, or butyl of the general formula $C_nH_{2n+1}$ and where x is a positive integer.

4. Condensed B-triamino-N-tris(trimethylsilyl)borazines, singly and doubly bridged and mixtures thereof

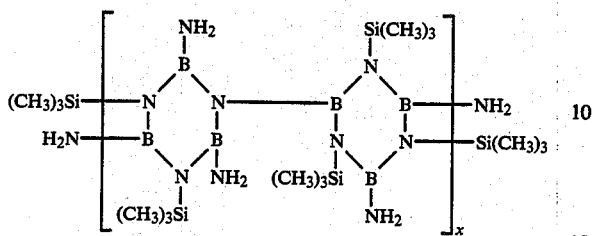

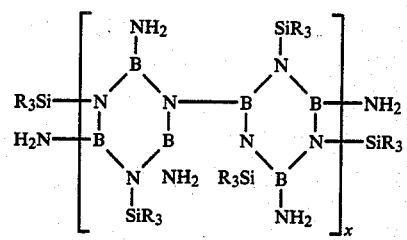

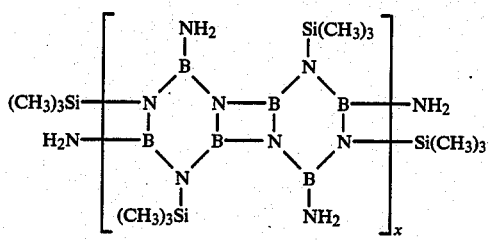

where x = 1, 2, 3, 4, 5, 6, 7, 8.

5. A method for condensing B-triamino-N-tris(trialkylsilyl)borazines and their dimers, trimers, tetramers, and octamers having the formula where R is methyl, ethyl, or butyl of the general formula $C_nH_{2n+1}$ and where x is a positive integer from 1 to 8, into preceramic polymers by gradual heat treatment from about 50° C. to 300° C. over a period of time varying from about 8 hr to 250 hr in an inert atmosphere.

6. The method of claim 8 wherein the compounds are condensed B-triamino-N-tris(trimethylsilyl)borazines, singly and doubly bridged and mixtures thereof.

7. The process of claim 6 further comprising heating the preceramic polymers in an ammonia atmosphere from about 60° C. to 1000° C. over time periods from about 8 hours to 27 days to form carbon-free boron nitride.

8. The process of claim 5 further comprising heating the preceramic polymers in an ammonia atmosphere from about 60° C. to 1000° C. over time periods from about 8 hours to 27 days to form carbon-free boron nitride.

* * * * *